(12) United States Patent
Knowles et al.

(10) Patent No.: US 7,544,164 B2
(45) Date of Patent: Jun. 9, 2009

(54) ULTRASOUND PROBES WITH IMPROVED ELECTRICAL ISOLATION

(75) Inventors: Heather Knowles, Devens, MA (US); Jacquelyn Byron, Arlington, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/599,727

(22) PCT Filed: Apr. 4, 2005

(86) PCT No.: PCT/IB2005/051107

§ 371 (c)(1), (2), (4) Date: Oct. 6, 2006

(87) PCT Pub. No.: WO2005/096950

PCT Pub. Date: Oct. 20, 2005

(65) Prior Publication Data

US 2007/0239017 A1    Oct. 11, 2007

Related U.S. Application Data

(60) Provisional application No. 60/560,479, filed on Apr. 8, 2004.

(51) Int. Cl.
*A61B 8/14* (2006.01)
(52) U.S. Cl. .................................................. 600/459
(58) Field of Classification Search ................ 600/459, 600/462, 466
See application file for complete search history.

(56) References Cited

U.S. PATENT DOCUMENTS

| 4,523,122 | A | * | 6/1985 | Tone et al. ................... 310/334 |
| 5,320,104 | A | | 6/1994 | Fearnside |
| 5,368,036 | A | | 11/1994 | Tanaka |
| 5,469,852 | A | * | 11/1995 | Nakamura et al. .......... 600/463 |
| 5,620,479 | A | * | 4/1997 | Diederich ....................... 601/3 |
| 5,886,454 | A | * | 3/1999 | Ito et al. ....................... 310/322 |

* cited by examiner

*Primary Examiner*—Eric F Winakur
*Assistant Examiner*—Michael T Rozanski

(57) ABSTRACT

Ultrasound probe (10) with improved electrical isolation including a housing (12), a sensor assembly (16) arranged in the housing (12) and including electrically conductive parts (22) which transmit, receive and process waves and an acoustic matching layer (34, 44) arranged in the housing (12) to electrically isolate the electrically conductive parts (22) from the housing (12). The matching layer (34, 44) serves as a barrier between the electrically conductive parts (22) and seams (30, 36, 40) formed between two parts (26, 28) of the housing (12) and/or between the housing (12) and another component connected thereto, e.g., an acoustic window (18) or a connection member (42) arranged at a rear of the housing (12). The invention thus increases the safety of the probe (10) in that it substantially reduces the risk to patients of an electrical shock. By using the matching layer (34, 44) to provide electrical isolation, the acoustics of the sensor assembly (16) are not interfered with, i.e., the waves being transmitted and received by the sensor assembly (16) are influenced in a desired manner.

16 Claims, 3 Drawing Sheets

ULTRASOUND PROBES WITH IMPROVED ELECTRICAL ISOLATION

The present invention relates generally to ultrasound probes and more particularly to ultrasound probes which provide improved electrical isolation of electrically conductive parts of a sensor assembly.

The present invention also relates to a method for manufacturing an ultrasound probe which provides reliable electrical isolation despite variations in the manufacturing process.

Ultrasound probes include assemblies which contain various live electrical parts (for example, pathways that create and return electrical signals) and ground parts which provide RFI immunity that are necessary for them to function in their intended manner. For patient safety and to meet the requirements of an industry standard designated IEC-60601, the patient must be fully isolated from any electrical/ground pathways within the probe. This electrical isolation must remain intact when the probe is exposed to stresses which arise in normal use, e.g., chemical exposure, heat and mechanical wear, as well as pass a variety of multiple fault conditions, e.g., a very high voltage differential between the probe and the patient.

For ultrasound probes for external body use, which generally do not have restrictive space constraints, these requirements are relatively easy to satisfy with proper material selection and design of the components of the housing of the probe. The probe can thus easily meet electrical creepage and clearance limitations (which relate to the path-length to reach electrical live parts). Currently, however, there is trend to design external-use ultrasound probes in consideration of ergonomics and this introduces restrictions on space constraints.

However, for ultrasound probes for internal body use, there are often tight space constraints so that the designs for ultrasound probes for external body use cannot be used in order to meet the electrical isolation requirements. In particular, for ultrasound probes designed for intra-cavity usage, such as transesophageal echocardiographic ultrasound probes (hereinafter referred to as TEE probes), there are often extremely tight space constraints and in addition, there are material limitations in view of the continual environmental stresses which arise during normal intra-cavity use. In view of the limited space and limitations on material for internal use ultrasound probes in comparison to ultrasound probes for external body use, it is therefore a much greater design challenge to achieve the required electrical isolation in such internal use ultrasound probes, including in particular, TEE probes.

In some current TEE probes, electrical isolation is achieved by encapsulating the metal/live parts of the sensor assembly in a hard epoxy within the outside plastic housing. Referring to FIG. 3, part of a prior art TEE probe 100 is shown. The TEE probe 100 includes a plastic housing 102 formed from an upper housing part 104 and a lower housing part 106 and thereby defining a seam 108 therebetween which extends along the entire interface between the two housing parts 104, 106, a bending neck or sheath 110 connected to the rear end of the housing 102 and an acoustic window or lens 112 which is placed in an aperture formed in an upper housing part 104 of the housing 102. A peripheral seam 114 is formed between the acoustic window 112 and the upper housing part 104. The probe 100 also includes a sensor assembly 116 which has electrically conductive parts 118 and an acoustic matching layer 120 arranged adjacent the acoustic window or lens 112. The electrically conductive parts 118 are often potted with epoxy 122, i.e., the entire space between the housing 102 and the electrically conductive parts 118 is filled with epoxy.

One problem with the prior art TEE probe of the type described above is that the seam 108 where the two housing parts 104, 106 of the housing 102 are connected to one another represents a highly vulnerable area to bubbles or voids which may be contained within the epoxy 122 or which may be created during the potting procedure. Areas of the epoxy 122 including such bubbles or voids are electrically weakened since the bubbles and voids create a pathway or channel for electrical charge from the electrically conductive parts 118 to the seam 108. Such weakened areas can cause the probe 100 to fail isolation requirements, since electrical charge from the electrically conductive parts 118 will travel to the seam 104, and thus is a patient safety risk.

In addition, the window seam 114, where the acoustic window 112 is glued to the upper housing part 104, and the seam 124 where the bending neck 110 is connected to the housing 102 are similarly vulnerable areas.

The formation of such bubbles and voids arises from the manner in which the probe is manufactured, i.e., the potting of the sensor assembly 116 with epoxy 122. Since the potting of the sensor assembly 116 with epoxy 122 inherently varies for each probe, while some probes might not have any bubbles or voids, others manufactured in the same manner may have several bubbles or voids.

The inconsistent and random nature of the formation of bubbles and voids poses a problem since the probes are tested for electrical safety after manufacture. Those probes which include bubbles or voids often fail the electrical safety tests and require reworking to repair the areas with bubbles or voids in the epoxy.

It would be beneficial to be able to construct an ultrasound probe for internal body use which can be reliably manufactured without the risk of forming electrical pathways or channels between electrically conductive parts of the sensor assembly of the probe and any seams in the housing of the probe, and which would not interfere with the acoustic function of the sensor assembly.

It is an object of the present invention to provide a new ultrasound probe which provides improved electrical isolation, especially ultrasound probes for internal body use, e.g., an intra-cavity ultrasound probe, without interfering with the acoustics of the probe.

It is another object of the present invention to provide a new ultrasound probe which can be reliably manufactured without the risk of forming electrical pathways or channels between electrically conductive parts of the sensor assembly of the probe and any seams in the housing of the probe. In this regard, it is also an object of the invention to provide a method for manufacturing an ultrasound probe which provides reliable electrical isolation despite variations in the manufacturing process.

It is yet another object of the present invention to provide a new ultrasound probe in which electrically conductive parts are potted in an epoxy within a housing and which provides electrical isolation even in the presence of bubbles or voids in the epoxy.

In order to achieve these objects and others, an ultrasound probe in accordance with the invention includes a housing, a sensor assembly arranged in the housing and including electrically conductive parts which transmit, receive and process waves, and an acoustic matching layer arranged in the housing to electrically isolate the electrically conductive parts from the housing. Since the housing typically includes seams formed between two parts of the housing or between the housing and another component connected thereto, e.g., an acoustic window or lens or a connection member arranged at a rear of the housing, the acoustic matching layer serves as a barrier between the electrically conductive parts and the seams and thereby prevents electrical charge from passing out of the housing via the seams. The invention thus increases the safety of the probe in that it substantially reduces the risk to patients of an electrical shock.

Moreover, by using an acoustic matching layer to provide electrical isolation, the acoustics of the sensor assembly are not interfered with, i.e., the waves being transmitted and received by the sensor assembly are influenced in the desired manner.

The matching layer may be wrapped entirely around the electrically conductive parts and extend past a seam formed at a rear of the housing between the housing and a connection member, with a seam of the matching layer being formed at a bottom of the housing. Alternatively, the matching layer may be trimmed shorter and sealed around the electrically conductive parts.

A method for manufacturing an ultrasound probe with an acoustic matching layer as described above involves wrapping the acoustic matching layer over a sensor assembly, inserting the wrapped sensor assembly into a first housing part, attaching an acoustic window into an aperture in the first housing part or in a second housing part which mates with the first housing part, attaching the acoustic window to the wrapped sensor assembly, joining the first and second housing parts together and filling an epoxy between the first and second housing parts and the wrapped sensor assembly. The presence of bubbles or voids in the epoxy, which arise during the manufacturing process, does not result in any vulnerability in the areas of seams in the housing or between the housing and another component in view of the enclosure of the electrically conductive parts in the matching layer.

The presence of the matching layer over the seams in the probe increases the safety in the use of and reliability of the probe and also reduces the likelihood of the probe failing safety requirements relating to electrical isolation. Specifically, wrapping of the acoustic matching layer over the sensor assembly improves the reliability of the probe during use since the acoustic matching layer prevents chemicals which might harm the sensor assembly from coming into contact therewith and also isolates the sensor assembly from humidity and possible cracks in the epoxy and housing caused by mechanical damage. Accordingly, fluids which might pass through any seams in the housing are prevented from coming into contact with the sensor assembly by the epoxy, when functional, and the acoustic matching layer.

The invention, together with further objects and advantages thereof, may best be understood by reference to the following description taken in conjunction with the accompanying drawings wherein like reference numerals identify like elements.

Figure 1:
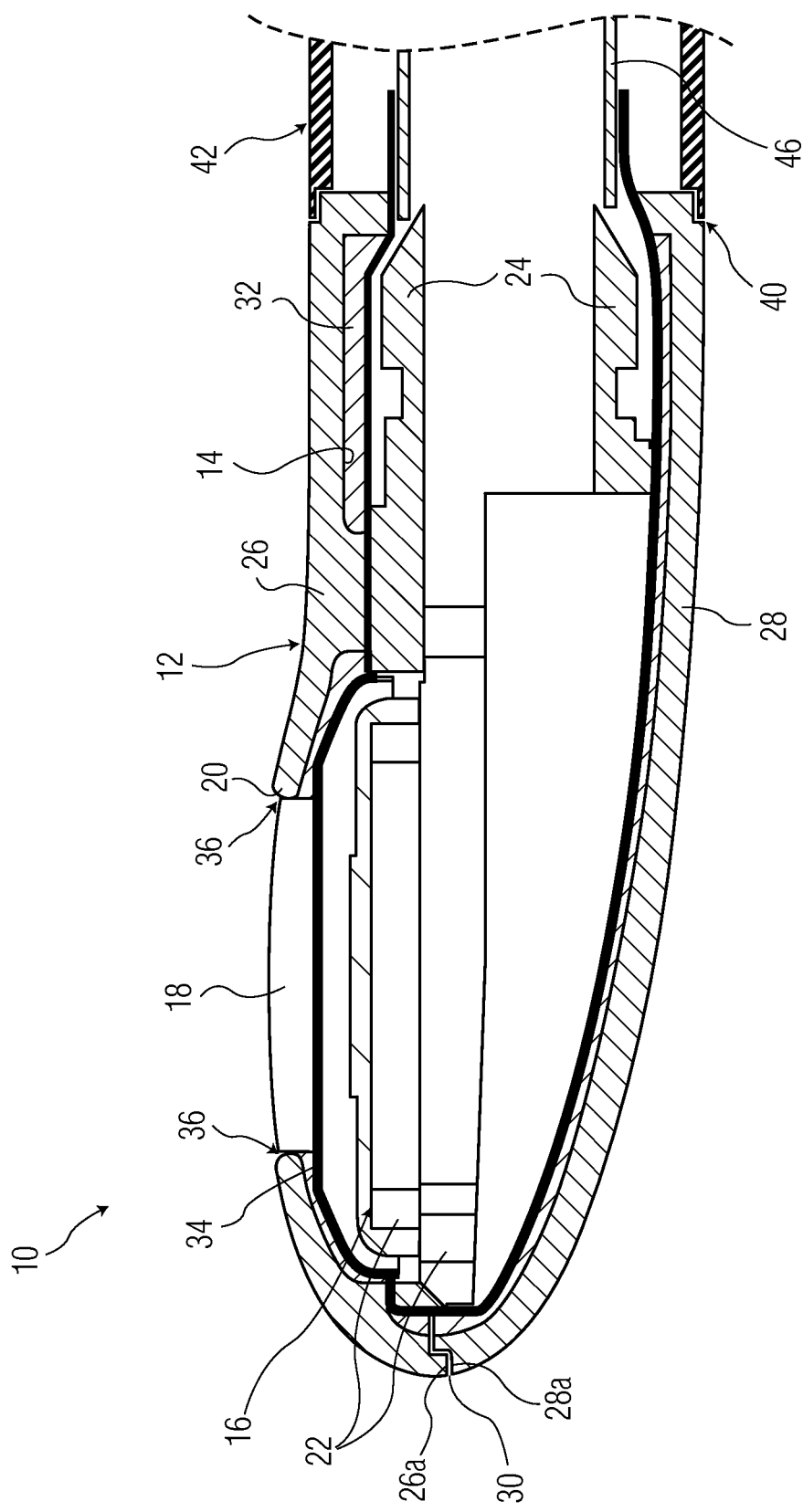
FIG. 1 is a cross-sectional view of a portion of a first embodiment of an ultrasound probe in accordance with the invention taken through the sensor assembly thereof.
Figure 2:
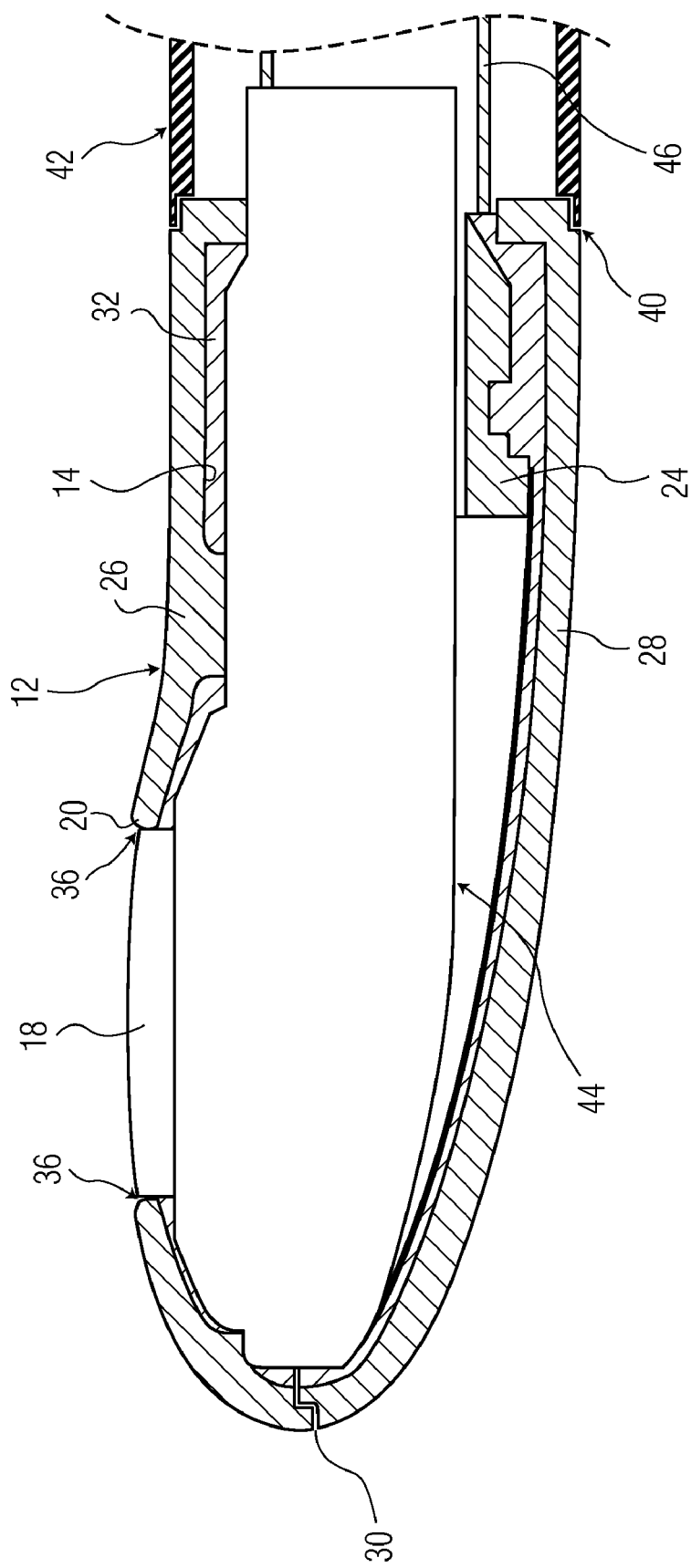
FIG. 2 is a cross-sectional view of a portion of a second embodiment of an ultrasound probe in accordance with the invention taken through the sensor assembly thereof.
Figure 3:
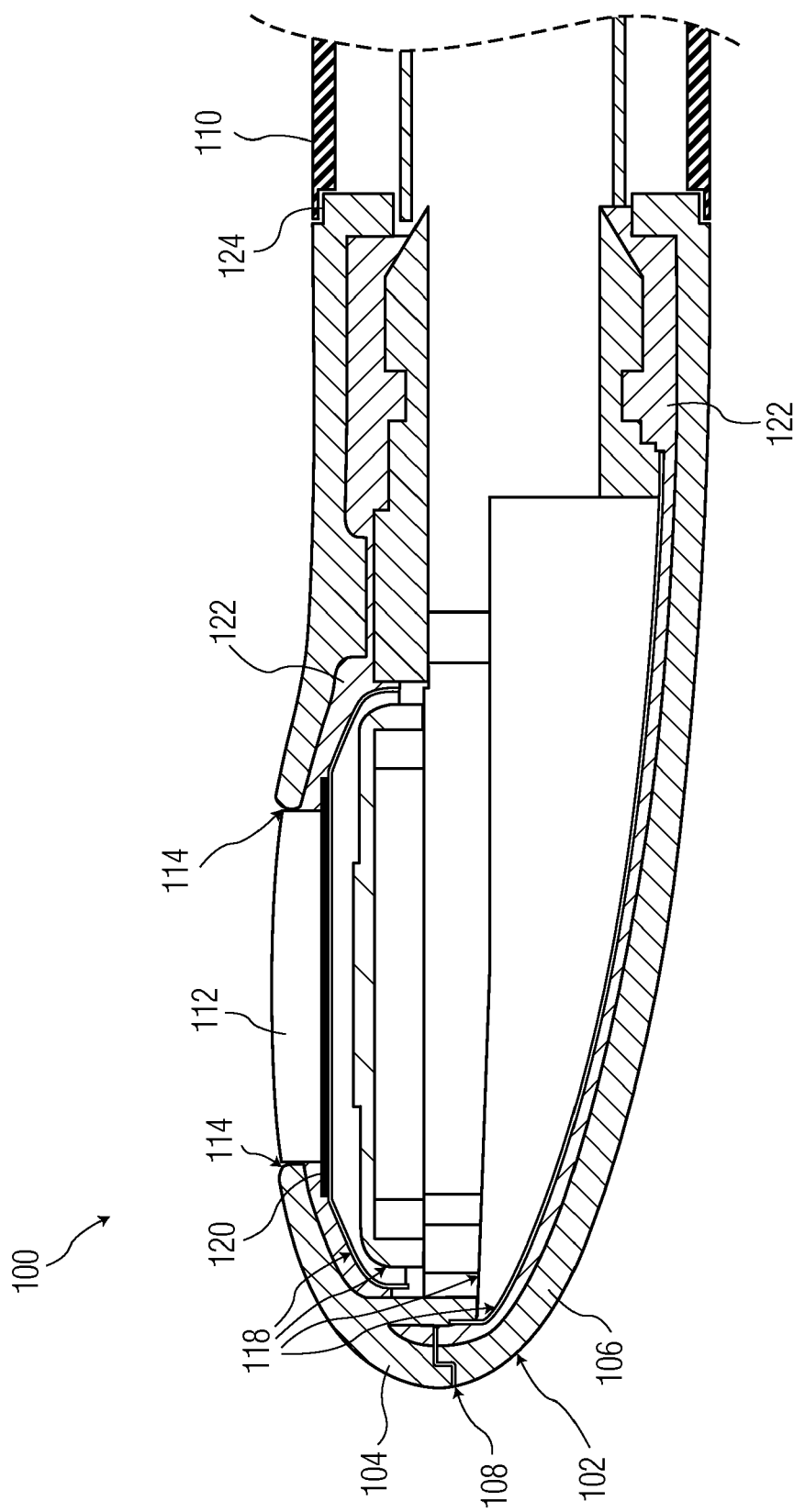
FIG. 3 is a cross-sectional view of a portion of a prior art TEE probe taken through the sensor assembly thereof.

Referring to FIGS. 1 and 2 wherein like reference numerals refer to the same or similar elements, an ultrasound transducer probe 10 in accordance with the invention includes a dielectric (plastic) housing 12 defining a cavity 14, an ultrasound sensor assembly 16 arranged in the cavity 14 and an acoustic window or lens 18 arranged in an aperture 20 of the housing 12. Sensor assembly 16 includes electrically conductive parts 22, including for example, parts of a transducer array arranged to align with the acoustic window or lens 18, and is supported in the housing 12 by dielectric sensor support parts 24.

Housing 12 includes an upper housing part 26 in which the aperture 20 for the acoustic window or lens 18 is formed and a lower housing part 28. Peripheral edges 26a, 28a of the upper and lower housing parts 26, 28, respectively, are designed to mate with one another to thereby form a seam 30 of the housing 12 therebetween. Formation of the housing 12 from two housing parts 26, 28 enables the probe 10 to be assembled by inserting the sensor assembly 16 into one housing part and then connecting the other housing part thereto. However, it is a drawback that, as mentioned above, the presence of the seam 30 leads to potential problems because the area in the vicinity of the seam 30 is highly vulnerable to bubbles and voids which may be contained within encapsulation epoxy 32 filling areas of the interior of the housing 12 not occupied by other components. The epoxy 32 is filled into the areas between the housing 12 and the sensor assembly 16 during the manufacture of the probe 10. If situated in the path of the electrical charge from the electrically conductive parts 24, the bubbles or voids would convey the electrical charge to the seam 30 and potentially inflict damage on the patient if the probe 10 is in use in the patient's cavity.

To substantially eliminate this risk of conveying electrical charge via bubbles or voids in the epoxy 32, in accordance with the invention, an acoustic matching layer 34 is wrapped over the electrically conductive parts 22 of the sensor assembly 16 to provide electrical isolation for the electrical conductive parts 22. In addition to being interposed between the sensor assembly 16 and the acoustic window or lens 18 (in which location an acoustic matching layer is present in prior art constructions), the acoustic matching layer 34 extends past the seam 30, i.e., from the location between the sensor assembly 16 and the acoustic window or lens 18 to a location alongside the lower housing part 28 below the seam 30. The acoustic matching layer 34 thereby extends across the seam 30, i.e., on both sides thereof. The acoustic matching layer 34 may be coated with an electrically insulative material. By wrapping the acoustic matching layer 34 around the electrically conductive parts 22 of the sensor assembly 16, the acoustic matching layer 34 serves a dual purpose, namely, as a conventional acoustic matching layer in the processing of waves generated and received by the sensor assembly 16 and as an electrical isolator for isolating the electrically conductive parts 22 in order to prevent electrical charge from being conveyed through any bubbles or voids in the epoxy 32 to the seam 30. The acoustic matching layer 34 thereby acoustically influences the waves transmitted and received by the sensor assembly 16 in the desired manner and does not interfere with the wave transmission and reception. Also, the presence of the acoustic matching layer 34 between the source of electrical charges, i.e., the electrically conductive parts 22, and the seam 30, increases the distance between the electrically conductive parts 22 and the seam 30 which improves the safety and reliability of the probe 10 vis-a-vis its meeting or exceeding creepage and clearance requirements. Moreover, even if the probe 10 does not meet creepage and clearance requirements, it is substantially improved regarding electrical isolation.

In addition to the seam 30, there are other points of discontinuity in the housing 12, including a seam 36 between the acoustic window or lens 18 and the aperture 20 in the upper housing part 26 in which the acoustic window or lens 18 is received. The acoustic matching layer 34 is therefore extended to be interposed between the electrically conductive parts 22 of the sensor assembly 16 and the seam 36. The acoustic matching layer 34 would thus be extended both forward toward the seam 30 to extend past the seam 30 to a location alongside the lower housing part 28 and rearward to extend until the dielectric sensor support parts 24.

In consideration of the foregoing, at a minimum, in an ultrasound probe constructed applying the electrical isolation techniques in accordance with the invention, the acoustic matching layer 34 should extend over any discontinuities in the housing 12, including but not limited to a seam formed between the upper and lower housing parts 26, 28 (or any mating housing parts) and the seam 36 formed between the acoustic window or lens 18 and the upper housing part 26. In the embodiment illustrated in FIG. 1, the acoustic matching layer 34 extends over the entire sensor assembly 16, over the sensor support parts 24 and out past the rear end 38 of the housing 12. In this manner, the acoustic matching layer 34 also protects a seam 40 formed between the rear end 38 of the housing 12 and the bending neck or sheath 42 which is connected to the housing 12, i.e., interposes an electrical isolation barrier between the electrically conductive parts 22 and the same 40. Constructed in this manner, the acoustic matching layer 34 has a closed front end alongside the seam 30 and an open rear end adjacent the sensor support parts 24, and into which an internal part of the bending neck 42 and/or cable 46 connecting the probe to a control system extends as shown in FIG. 1. The acoustic matching layer 34 thereby defines an elongate cavity in which the electrically conductive parts 22 are enclosed and isolated from the seams in the housing 12 (seam 30) and between the housing 12 and other components, i.e., the acoustic window or lens 18 (seam 36) and the bending neck or sheath 42 (seam 40).

A bending neck or sheath 42 is typically present in TEE probes. In other intra-cavity probes in which the isolation technique described above can be applied, such a bending neck or sheath may not be present but rather, another connection member is connected to the rear end of the probe housing, such as a strain relief member or cable jacket, and encloses one or more cables which attach the probe to the control system. The acoustic matching layer for these probes would thus extend circumferentially from a location in the probe housing to a location in the connection member to thereby extend across the seam between the housing and the connection member.

Referring now to FIG. 2, in an alternate embodiment, the acoustic matching layer 44 is trimmed so that it does not wrap completely around the bottom of the sensor assembly 16 (not shown in FIG. 2). Specifically, the acoustic matching layer 44 is trimmed below the seam 30 of the housing 12 and passed inward of the sensor support parts 24 so that the electrically conductive parts 22 (not shown in FIG. 2) are still electrically isolated from the seam 12 as in the embodiment shown in FIG. 1. An advantage is obtained in that reduction of the extent of the acoustic matching layer 44 on the underside the sensor assembly 16 enables the probe 10 to be built easier. The trimmed acoustic matching layer 44 is retained against by the sensor support parts 24 and optionally may be connected thereto Generally, any acoustic matching layer which provides electrical isolation and has desired acoustic properties can be used in the invention. The inclusion of a protective electrical covering in the acoustic matching layer does not comprise the wave transmission and reception by the sensor assembly 16.

A preferred acoustic matching layer is a parylene-coated acoustic layer of polyurethane which provides extreme electrical isolation (about 4000 V). Alternatively, other flexible plastics, such as polyolefins and thermoplastic elastomers that are appropriate for use as acoustic matching layers, can be used with or without a parylene coating.

Housing 12 can be shaped in the form of any type of TEE, transthoracic, intra-cavity, intra-operative, transnasal or endocavity probe. Depending on the type of probe, the upper and lower housing parts 26, 28 are shaped so that when combined, the housing 12 assumes the shape of the desired probe. Housing 12 and the sensor assembly 16 in accordance with the invention can also be used in any imaging device in the medical field. Thus, the sensor assembly 16 represents any type of imaging apparatus.

With ultrasound probes applying the isolation technique described above, the probe manufacturing process is improved in that it becomes possible to almost ensure that the probes will satisfy electrical safety tests. Reworking of the probes would then not be required. The manufacturing process would entail wrapping the sensor assembly 16 with an acoustic matching layer 34, inserting the wrapped sensor assembly into one housing part, attaching the acoustic window or lens 18 into the aperture 20 in the upper housing part 26 and to the wrapped sensor assembly and then joining the housing parts 26, 28 together. The epoxy 32 is filled into the space between the housing 12 and the wrapped sensor assembly. An ultrasound probe 10 manufactured in this manner would likely meet standard safety requirements even if bubbles are present in the epoxy 32.

The invention is particularly suited for use in intra-cavity or internal-use ultrasound probes in view of space constraints in such probes. However, it is equally applicable for external-use probes since by using the invention, it becomes possible to provide a single material which electrically isolates the sensor assembly and also provides desired acoustic influences to the waves being transmitted and received by a sensor assembly.

Although illustrative embodiments of the present invention have been described herein with reference to the accompanying drawings, it is to be understood that the invention is not limited to these precise embodiments, and that various other changes and modifications may be effected therein by one of ordinary skill in the art without departing from the scope or spirit of the invention.

The invention claimed is:

1. An ultrasound probe, comprising:
   a housing including a plurality of seams, each of which extends from an exterior of said housing to an interior of said housing;
   a sensor assembly arranged in said housing and including electrically conductive parts, said sensor assembly being arranged to transmit and receive waves; and
   an acoustic window along a side of the housing;
   an acoustic matching layer arranged in said housing between said electrically conductive parts of said sensor assembly and each of the seams, wherein one of the seams is not along the side of the acoustic window, said acoustic matching layer being arranged to acoustically influence waves transmitted and received by said sensor assembly in a desired manner.

2. The probe of claim 1, wherein said matching layer is arranged entirely around said electrically conductive parts of said sensor assembly.

3. The probe of claim 1, wherein said housing comprises first and second housing parts with a seam being formed therebetween, said matching layer extending from a location alongside said first housing part to a location alongside said second housing part and thereby extending across said seam between said first and second housing parts.

4. The probe of claim 1, wherein the acoustic window is arranged in an aperture of said housing such that one of the seams is formed between said housing and said acoustic window, said matching layer extending from a location adjacent said acoustic window to a location alongside said housing outward from said aperture and thereby extending across said seam between said housing and said acoustic window.

5. The probe of claim 1, further comprising epoxy arranged between said matching layer and said housing.

6. The probe of claim 1,
wherein the acoustic window arranged in an aperture at a front portion of said housing, said electrically conductive parts being arranged at least partially opposite said acoustic window; and the probe further comprises:
dielectric sensor support parts arranged at a rear portion of said housing to support said electrically conductive parts, said matching layer having a closed front end and an open rear end adjacent said sensor support parts and defining an elongate cavity in which said electrically conductive parts are enclosed.

7. The probe of claim 1, wherein said matching layer is arranged to wrap over said electrically conductive parts in their entirety.

8. The probe of claim 1, further comprising a connection member connected to a rear end of said housing and defining a seam therebetween, said matching layer being arranged to extend across said seam between said connection member and said housing.

9. The probe of claim 1, wherein said matching layer comprises parylene-coated polyurethane.

10. The probe of claim 1, wherein said matching layer comprises one of a polyolefin or a thermoplastic elastomer.

11. The probe of claim 1, wherein said housing is in the form of a housing for a transesophageal echocardiographic ultrasound probe.

12. The probe of claim 1, wherein said matching layer is coated with an electrically insulative material.

13. An ultrasound probe, comprising:
a housing (12);
an acoustic window;
a sensor assembly arranged in said housing and including electrically conductive parts, said sensor assembly being arranged to transmit and receive waves;
an acoustic matching layer wrapped around said electrically conductive parts to electrically isolate said electrically conductive parts from said housing, said acoustic matching layer being arranged to acoustically influence waves transmitted and received by said sensor assembly in a desired manner; and
a connection member connected to a rear end of said housing and defining a seam therebetween, said matching layer being arranged to extend across said seam between said connection member and said housing.

14. The probe of claim 13, wherein said matching layer defines an elongate cavity having a closed front end adjacent a tip of said housing and an open rear end, said electrically conductive parts being arranged in said cavity.

15. The probe of claim 14, further comprising dielectric sensor support parts arranged at a rear portion of said housing to support said electrically conductive parts, said rear end of said matching layer being situated adjacent said sensor support parts.

16. The probe of claim 13, wherein said matching layer comprises parylene-coated polyurethane.

* * * * *